United States Patent [19]

Schiller

[11] Patent Number: 4,862,488
[45] Date of Patent: Aug. 29, 1989

[54] DEVICE FOR MEASURING THE ORIENTATION OF BULK MONOCRYSTALLINE MATERIALS USING THE LAUE METHOD

[75] Inventor: Claude Schiller, Savigny-sur-Orge, France

[73] Assignee: U.S. Philips Corporation, New York, N.Y.

[21] Appl. No.: 17,391

[22] Filed: Feb. 20, 1987

[30] Foreign Application Priority Data

Mar. 18, 1986 [FR] France ................ 86 03818

[51] Int. Cl.$^4$ ........................................... G01N 23/20
[52] U.S. Cl. .................................... 378/81; 378/79; 378/76; 378/73; 378/71
[58] Field of Search ............... 378/70, 71, 73, 76, 378/79, 80, 81; 437/8, 226

[56] References Cited

U.S. PATENT DOCUMENTS

| | | | |
|---|---|---|---|
| 2,904,688 | 9/1959 | Miller | 378/76 |
| 3,078,559 | 2/1963 | Thomas | 437/226 |
| 3,566,112 | 2/1971 | Luecke | 378/81 |
| 3,631,239 | 12/1971 | Krieder | 378/76 |
| 4,217,493 | 8/1980 | Li et al. | 378/73 |
| 4,228,578 | 10/1980 | Lin et al. | 437/226 |
| 4,547,958 | 10/1985 | Hufford | 437/8 |
| 4,710,259 | 12/1987 | Howe et al. | 378/73 |
| 4,788,702 | 11/1988 | Howe et al. | 378/71 |

FOREIGN PATENT DOCUMENTS

| | | | |
|---|---|---|---|
| 0217889 | 1/1985 | Fed. Rep. of Germany | 378/70 |
| 0805419 | 2/1981 | U.S.S.R. | 378/73 |

*Primary Examiner*—Janice A. Howell
*Assistant Examiner*—John C. Freeman
*Attorney, Agent, or Firm*—Paul R. Miller

[57] ABSTRACT

Device for measuring the orientation of bulk monocrystalline materials with respect to the crystallographic parameters using the Laue method, consisting, on the one hand, of a Laue chamber including a polychromatic x-ray source, a photographic film support and a collimator placed in the path of the x-rays between the source and the film in the vicinity of the latter defining the optical axis of the Laue chamber, and consisting, on the other hand, of means of support for a bulk specimen, of means of alignment for the chamber and the means of support, and means of determining the orientation of the specimen with respect to the crystallographic axes, characterized in that the means of support comprise at least one specimen-carrier which has a first planar face to receive the specimen, a second planar space perpendicular to the first for immobilizing the specimen, a first reference plane parallel to the first planar face, a second reference face parallel to the second planar face and a third reference plane perpendicular to both the first and the second planar faces, in that the means of alignment consist of an optical bench having at least two planar reference faces which are parallel to the optical axis of the Laue chamber, and in that the means of support and the means of alignment interact to provide the means for determining the orientation of the specimen, because, during the measurement, the first and the second reference planes of the optical bench support the combination chosen from the first and the second, or alternatively the first and the third, reference planes of the specimen-carrier.

7 Claims, 9 Drawing Sheets

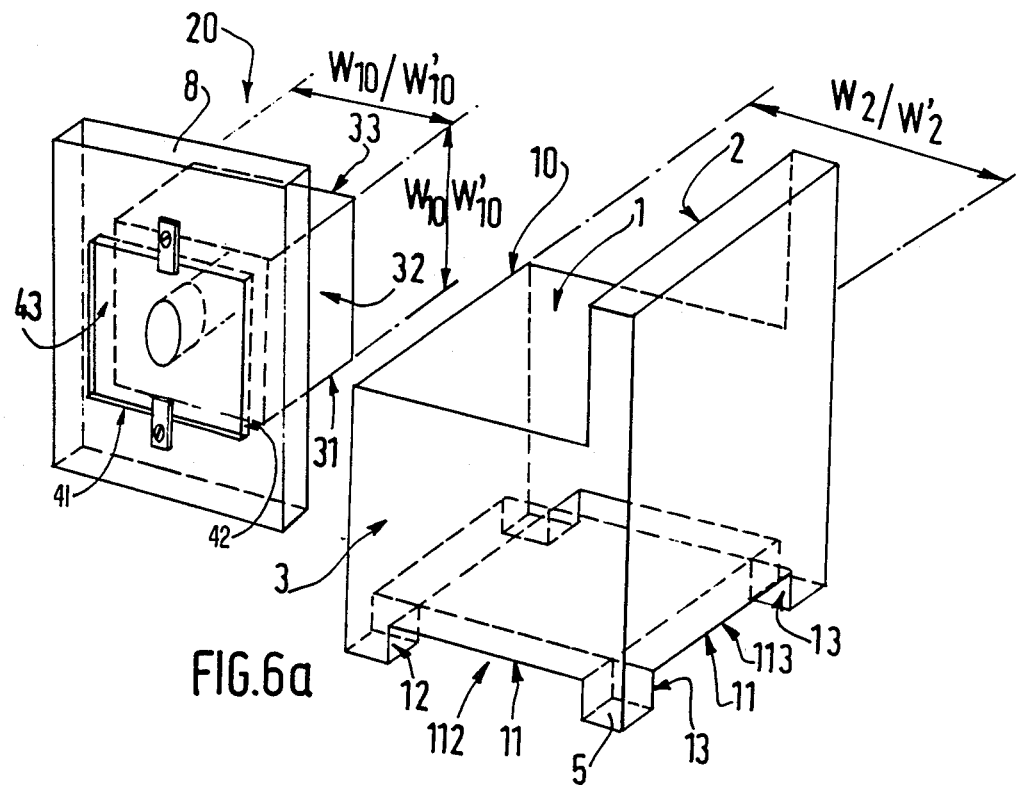
FIG.6a
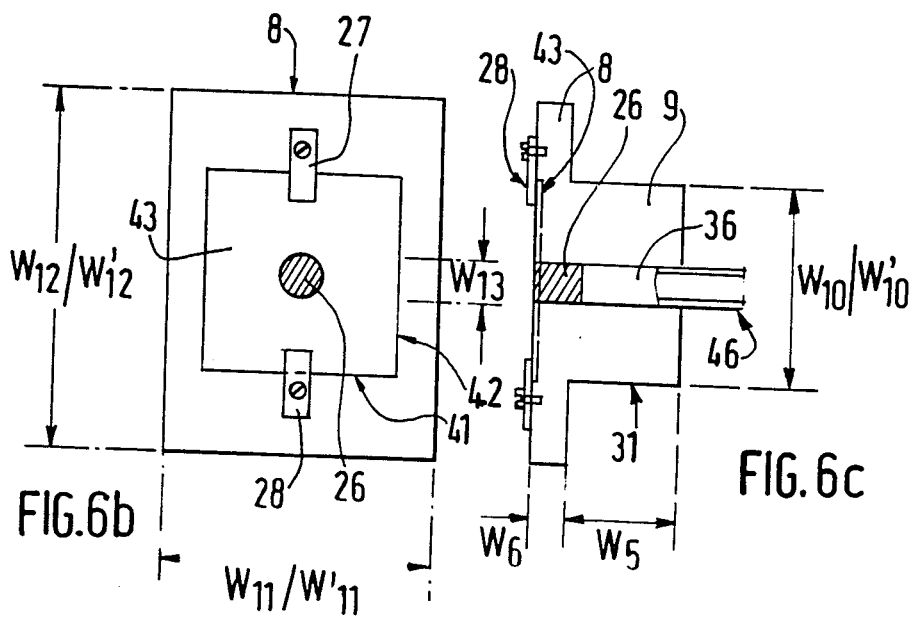
FIG.6b
FIG.6c

DEVICE FOR MEASURING THE ORIENTATION OF BULK MONOCRYSTALLINE MATERIALS USING THE LAUE METHOD

The invention relates to a device for measuring the orientation of bulk monocrystalline materials in relation to the crystallographic parameters by means of the Laue method, consisting, on the one hand, of a Laue chamber containing a polychromatic x-ray source, a photographic film support and a collimator placed in the path of the x-rays between the source and the film in the vicinity of the latter, defining the optical axis of the Laue chamber, and consisting, on the other hand, of means of support for a bulk specimen, means of alignment for the chamber and means of support, and means for determining the orientation of the specimen in relation to the crystallographic axes.

The invention also relates to a process for producing a semiconductor device from a semiconductive, bulk monocrystalline billet making use of this device.

The invention finds its application in the measurement of the orientation of single crystals of new materials such as, for example, semiconductors, in order to form crystals used as seeds for pulling or in order to form wafers of substrates intended to receive expitaxial layers, for which orientation an extreme accuracy is required. The invention finds an application most particularly in the orientation of single crystals of III-V compounds such as, for example, gallium arsenide.

The so-called Laue method is well known in the state of the art, for example from the publication entitled "Introduction to Solid-State Physics" by Kittel, published by Dunod, pages 50–51.

According to this method, a single crystal is held stationary in a polychromatic x-ray beam. The crystal diffracts only the waves of wavelengths for which there exist lattice planes which are separated by a distance and inclined in relation to the beam at an angle such that Bragg's Law is obeyed. Each crystal plane selects from the incident beam a wavelength corresponding to Bragg's equation. The pattern obtained by the Laue method consists of spots whose arrangement is characteristic of the crystal symmetry, and it may be employed for orienting the single crystal in relation to the crystallographic parameters.

A device for implementing the Laue method is known from U.S. Pat. Nos. 2,495,111, 2,543,160, 2,933,993, 2,483,389, 2,854,908 and others, filed by the Polaroid company between 1949 and 1954. In addition to a support for a film, this device comprises a collimator consisting of a tube fitted with a diaphragm at each end, fastened on a support at right-angles to the film and at a small distance from one of the faces of the latter, and a screen, known as a transformation screen, fastened on the support in parallel to the film and at a small distance from the other face of the latter. This transformation screen converts the x-ray photons into visiblelight photons for better utilization of the Polaroid negative films which are not very sensitive to X-rays.

To produce a Laue pattern by means of this known device, a polychromatic beam generated by an x-ray source is directed onto the collimator, and passes through the collimator, the negative film and then the transformation screen, through a circular opening made in the latter, before striking the crystal under study. The x-ray beam thus produces on the film a spot which marks the path of the direct beam and which materializes the optical axis of the device. The rays reaching the crystal are diffracted by surface crystal planes and return toward the negative film support. On returning, therefore, the diffracted rays strike the transformation screen which converts the x-ray photons into visible-light photons, which, in their turn, mark the negative film, forming the diffraction pattern of the single crystal, a pattern whose central spot consists of the spot due to the direct beam of x-rays.

The measurements which yield the orientation of the crystal under study, in relation to the crystallographic parameters, are performed using the pattern produced on the negative film, or a positive print of the negative film.

It is clear that in order to obtain very accurate information concerning the orientation of the crystal, the optical alignment of the whole system consisting of the Laue chamber and the crystal must be highly accurate.

In point of fact, the known device permits the various elements, such as, for example, the film support, to only be installed relatively inaccurately, and provides no information concerning the placing of the crystal to be characterized.

The document "Introduction to Solid-State Physics", cited as the state of the art, suggests placing the specimen on a goniometer stage. However, a mounting of this kind is slow to implement and contrary to systematic accurate measurements which must be used in the manufacture of semiconductor devices from single crystals, for example.

This is why the present invention offers both a measurement device and method which enable these problems to be solved.

According to the invention, these problems are solved with the aid of a device such as is described in the preamble, characterized in that the means of support comprise at least one specimen-carrier which has a first planar face to receive the specimen, a second planar face perpendicular to the first for immobilizing the specimen, a first reference plane parallel to the first planar face, a second reference plane parallel to the second planar face and a third reference plane perpendicular both to the first and to the second planar faces, in that the means of alignment consist of an optical bench having at least two planar reference faces which are parallel to the optical axis of the Laue chamber, and in that the means of support and means of alignment interact to provide the means for indicating the orientation of the specimen because, during the first measurement, the first and the second reference planes of the optical bench support the combination chosen from the first and the second, or alternatively the first and the third, reference planes of the specimen-carrier.

This device may additionally be characterized in that, when the first and the second reference planes of the optical bench support the combination of the first and the second reference planes of the specimen-carrier, the first planar face and the second planar face of this specimen-carrier are adjusted with respect to the optical axis of the Laue chamber to a distance from this axis which is substantially equal to the mean radius of the specimen.

This device may also be characterized in that the means of support additionally comprise a disc-carrier which has a first planar face, a second planar face perpendicular to the first for supporting and immobilizing the slice of a monocrystalline disc cut from a billet, a third planar face perpendicular to the first two to receive one of the faces of the disc, a first reference plane parallel to the first planar face, and a second reference plane parallel to the second planar face, and in that the disc-carrier interacts with the specimen-carrier and with the means of alignment to provide the means for determining the orientation of the disc, because, during the measurement, the first and the second reference planes of the disc-carrier rest against the first and the second planar faces of the specimen-carrier, and because the first and the second reference planes of the optical bench support the first and the third reference planes of the specimen-carrier.

The device according to the invention offers numerous advantages including, among others:

the fact of being simple and inexpensive to make, the fact of permitting highly accurate orientations to better than 0.1° with respect to a crystallographic axis or face. In fact, in this device, the placing of the movable elements, such as, for example, the film, does not affect the result of the measurement in any way, this measurement being made in relation to reference planes which are machined mechanically with a high accuracy and placed so that they are fixed in relation to the optical axis, the fact of permitting repetitive and systematic measurements, that is to say a large-scale industrial application which is competitive in cost, and the fact of permitting the orientation of the billet in relation to a generatrix of the cylinder. This operation makes it possible, in fact, to obtain directly any existing disorientation of the large flat plane and constitutes one of the critical stages in the preparation of the material for its industrial use, that is to say, for example, for the preparation of the substrate for an integrated circuit.

The invention will be understood better with the aid of the following description, illustrated by the attached figures, including:

FIG. 1 which shows a Laue chamber in diagrammatic section in parallel to the optical axis, FIG. 2a which shows, in perspective, the specimen-carrier for monocrystalline billets, according to the invention, FIG. 2b which shows a section of the specimen-carrier for 51 mm diameter billets, FIG. 2c which shows a section of the specimen-carrier for 76 mm diameter billets.

FIG. 2d which shows the rear of the specimen-carrier in plan view,

FIG. 3a which shows the optical bench in perspective,

FIG. 3b which shows the mounting of the specimen-carrier on the optical bench for measurements along a generatrix of the billet, FIG. 3c which shows the mounting of the specimen-carrier on the bench for a measurement on a billet face perpendicular to the pulling axis, FIG. 4a which shows a billet of raw gallium arsenide after pulling, FIG. 4b which shows the position of the diffraction spots in a Laue pattern obtained on a face of the gallium arsenide billet perpendicular to the [100] axis of pulling, FIG. 4c which shows a billet of this kind on which a large flat reference face has been produced, FIG. 4d which shows the position of the diffraction spots in a Laue diagram obtained on a generatrix of the gallium arsenide billet parallel to the [100] axis of pulling and perpendicular to the [$0\bar{1}1$] axis, FIG. 4e which shows a billet of this kind which has been through an appropriate machining operation to make it cylindrical, and on which a large flat face perpendicular to the [011] axis and a small flat face perpendicular to the [$0\bar{1}1$] axis have been produced, FIG. 4f which shows a disc cut from a cylinder of this kind, FIG. 5a which shows a billet of this kind mounted on the specimen-carrier in a position for measurement on a generatrix, FIG. 5b which shows a billet of this kind mounted on the specimen-carrier, in a position for measurement on an end face, FIG. 6a which shows the disc-carrier and the specimen-carrier, in perspective, FIG. 6b which shows the front view of the disc-carrier, and FIG. 6c which shows a section through the disc-carrier.

As shown diagrammatically in section in FIG. 1, the Laue chamber thus comprises:

a polychromatic x-ray source S, which may advantageously be a Philips-type PW 2224/20 source with a tungsten anticathode whose focus F is $0.4 \times 8$ mm in size and may be used at a take-off angle $\alpha$ of between 0° and 20°;

a collimator C intended to produce a fine direct beam of x-rays, consisting, for example, of a metal tube fitted with diaphragms $D_1$ and $D_2$ at each end;

a flat film P mounted in a support which is not shown; and a transformation screen T.

These elements are known to the person skilled in the art and, strictly speaking, do not form part of the invention.

As shown in FIG. 1, the x-rays originating from the source S pass through the collimator C and the transformation screen T through an opening $D_3$ with a diameter greater than the opening of the collimator diaphragms $D_1$ and $D_2$.

The rays then strike the specimen E. The rays reaching the specimen are diffracted, for example by a lattice plane R which forms an angle $\phi$ with the surface of the specimen E.

The diffracted rays then return toward the negative film support. On returning, they strike the transformation screen T which converts the x-ray photons into visible-light photons which, in their turn, leave their mark on the negative film, producing the diffraction pattern of the single crystal, a pattern whose central spot consists of the mark of the direct beam of x-rays.

The x-ray source S, the collimator C, the film-plane support P, the transformation screen T and a specimen-carrier for the specimen E are mounted on a high-precision optical bench, this bench itself being mounted on a "marble slab", also of high precision. These elements are, furthermore, aligned optically along the axis $X'''$.

The person skilled in the art knows that the monocrystalline specimens intended for industrial use are of standard shape and dimensions.

In most cases nowadays, these single crystals are semiconductors and may be, for example, germanium or silicon.

They may also consist of monocrystalline, group III-V compounds such as gallium arsenide, a compound which is relatively new when compared with silicon and in the case of which numerous problems still remain to be solved.

These single crystals of semiconductors of group IV such as germanium or silicon, or of group III-V such as gallium arsenide, are generally produced by being grown from a melt bath by a method of the Czochralski type, for example, from a carefully oriented pulling seed.

For their industrial application they must then be fashioned into the shape of a cylinder whose axis coincides with the pulling axis of the original billet.

In most cases this cylinder is of a standard diameter, expressed in the old Anglo-Saxon units, which is two inches, that is to say approximately 51 mm, or three inches, that is to say approximately 76 mm.

In addition, also for these industrial applications, these cylinders must have a reference flat face produced along a crystallographic face chosen by agreement between the manufacturers and the users.

From these cylinders, thin discs are then cut at right-angles to the axis of symmetry of the cylinder, for application in, for example, integrated circuits.

The trace of the flat face of the cylinder produces a cut facet on the discs, which permits the orientation of each disc to be determined, this orientation being of great importance, since, in general, these materials have anisotropic properties.

All these operations of fashioning of the cylinder, of the flat face, and of the wafers need to be performed with utmost accuracy with respect to the orientation of the axis of the cylinder, the orientation of the flat face, and the orientation of the parallel faces of the discs.

In point of fact, the accuracy of orientation of the cylinder axis determines the accuracy of the parallel faces of the discs and hence the quality of the layers, for example epitaxial or implanted, produced subsequently. The accuracy of orientation of the flat face determines the orientation of the active and passive devices produced on the discs used as a substrate for integrated circuits, and hence the performance of the circuits, since this performance depends on the orientation of the element, because of the anisotropy of the material properties.

The device which is known in the state of the art by the name of a Laue chamber makes it possible to determine the orientation of the single crystals which are subjected to this method.

However, for the application which is envisaged, this device needs to be improved, to provide:

measurements which are highly accurate, that is to say with an accuracy better than or equal to 0.1° with respect to the orientation, measurements which are highly reproducible, that is to say which do not depend on an adjustment, a placing or an optical alignment which is laborious and dependent on the knowledge and skill of the operator, and measurements which can be performed in the course of industrial manufacture, that is to say systematically and simply during the industrial manufacture of the billets and the discs resulting in the industrial manufacture of, for example, integrated circuits.

According to the invention, this objective is attained with the aid of the specimen-carrier shown in perspective in FIG. 2a.

This specimen-carrier 10 comprises a first planar face 1 and a second planar face 2 which is perpendicular to the first.

In the embodiment shown in FIG. 2a, these planar faces are machined with high accuracy from a massive block of metal.

This massive block of metal also has grooves 112 and 113 machined in its base, which determine a reference plane 11 parallel to the first planar face 1. These grooves also determine reference planes 12 and 13, reference plane 12 being parallel to the planar face 2 and reference plane 13 being perpendicular to both the planar faces 1 and 2. The grooves 112 and 113 thus determine, in the block 10, feet 5 of height h whose inner faces form the reference planes 12 and 13. The size of the grooves 112 and 113 is $W_4$. These grooves are intended to permit the specimen-carrier 10 to straddle an optical bench B shown in perspective in FIG. 3a.

As shown in this FIG. 3a, the optical bench B comprises a first reference plane 21, of size $W_4$, for supporting, on the one hand, the Laue chamber and, on the other hand, the specimen-carrier.

The Laue chamber is mounted onto the optical bench B in such a way that its optical axis X'X" is perpendicular to the dimension $W_4$ of the optical bench and parallel to its surface 21.

The optical bench B also comprises a second reference plane 22 perpendicular to plane 21. In these conditions, the specimen-carrier 10 may be placed on the optical bench in such a way that the reference plane 11 of the specimen-carrier rests on the reference plane 21 of the bench B and that either the reference plane 12 or, alternatively, the reference plane 13, rests against the reference plane 22 of the bench B.

The size of the grooves 112 and 113 is thus also made to be of dimension $W_4$, but with a clearance which is just sufficient for the specimen-carrier to slide on the optical bench B with, the feet 5 immobilizing the specimen-carrier on the bench. To this end, the dimension of the reference plane 22 of the optical bench, in parallel with the dimension h of the feet 5, is made greater than this dimension h.

Since the grooves 112 and 113 are made in two perpendicular directions, the specimen-carrier 10 can also be positioned on the bench B in two perpendicular directions, as shown in FIGS. 3b and 3c.

As shown in FIG. 3b, the specimen-carrier 10 is placed on the bench B so that the reference plane 11 rests on the reference plane 21 of the bench B, and the reference plane 13 rests against the reference plane 22. Since the optical axis X'X" is perpendicular to the dimension $W_4$ of the bench, it is then perpendicular to the planar face 2 of the latter.

This position of the specimen-carrier with respect to the bench B will be referred to throughout the description of the invention as the "transverse" position of the specimen-carrier on the bench.

As shown in FIG. 3c, the specimen-carrier 10 is placed on the bench B so that the reference plane 11 rests on the reference plane 21 of the bench B, and the reference plane 12 rests against the reference plane 22. Since the optical axis X'X" is perpendicular to the dimension $W_4$ of the bench, it is then parallel both to the planar face 2 and to the planar face 1 of the latter.

In the preferred embodiment of the invention shown in FIGS. 2 to 6, where the specimen-carrier is machined from a block 10 and all the faces are either parallel or perpendicular, the optical axis X'X" is then perpendicular to the planar face 3 shown in FIGS. 2a, 3b and 3c.

This last position of the specimen-carrier with respect to the bench B, illustrated in FIG. 3c, will be referred to throughout the description of the invention as the "lengthwise" position of the specimen-carrier on the bench.

The various dimensions of the specimen-carrier according to the invention for the applications are given in Table I by way of example of embodiment.

TABLE I

| Application 2" ≃ 51 mm | Application 3" ≃ 76 mm |
| --- | --- |
| $W_1 = 64.5$ mm | $W'_1 = 52$ mm |
| $W_2 = 63$ mm | $W'_2 = 76$ mm |
| $W_3 = 35.5$ mm | $W'_3 = 48$ mm |
| $W_4 = 56$ mm | $W'_4 = 56$ mm |
| $W_5 = 76$ mm | $W'_5 = 76$ mm |
| $W_6 = 10$ mm | $W'_6 = 10$ mm |
| $W_7 = 10$ mm | $W'_7 = 19$ mm |
| $W_8 = 13$ mm | $W'_8 = 9$ mm |
| $W_{10} = 51$ mm | $W'_{10} = 76$ mm |

The specimen-carrier according to the invention may be advantageously machined from a massive metal block of Dural (registered trademark), stainless steel or gold bronze.

The specimen-carriers are given such dimensions that in a lengthwise or transverse position the plane of symmetry of the reference face 1, which is the face carrying the specimen, coincides with the plane of symmetry of the optical bench, with that of the specimen and also contains the optical axis, the specimen being supported against the planar face 2.

In addition, these dimensions are made such that, in a lengthwise position, the first planar face 1 and the second planar face 2 are set at a distance from the optical X'X" which is substantially equal to the mean radius of the specimen.

A process for establishing the orientation of a massive billet with the aid of a Laue chamber equipped with the specimen-carrier according to the invention is described below, the bulk billet being a single crystal of gallium arsenide, taken as an example.

Figure 4A:
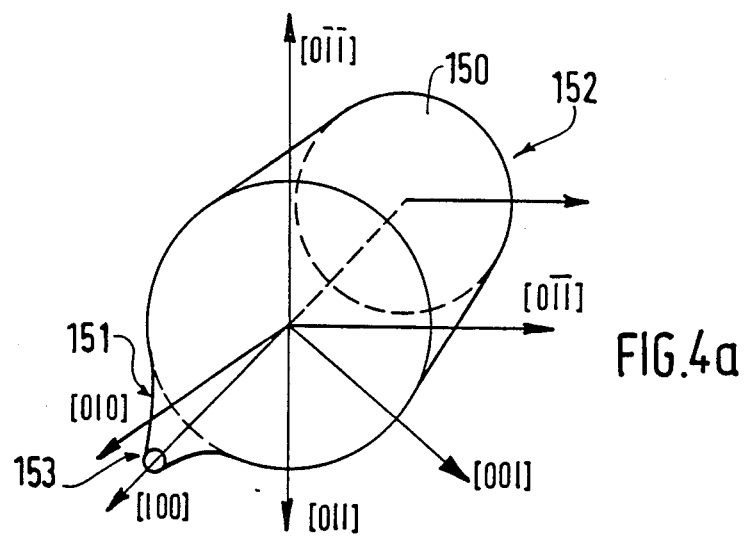

FIG. 4a shows a billet 150 of gallium arsenide, raw from pulling. This billet, which is approximately cylindrical, has a portion of smaller diameter which corresponds to the start of the pulling from a carefully oriented seed. This small-diameter part is known as the "head" 151 of the billet. The opposite end is known as the "tail" 152. In this example, the pulling takes place along the [100] crystallographic axis. The other crystallographic axes are then placed as shown in FIG. 4a, respectively.

A face 153 is first made at right angles to the pulling axis, on the head side of the billet, either by cleavage or by sawing.

The billet is placed on the specimen-carrier 10 so that the pulling axis is parallel both to faces 1 and 2. The billet rests against each of the faces 1 and 2, since it is almost cylindrical.

The specimen-cylindrical 10 is placed on the optical bench B in the "lengthwise" position. The faces 1 and 2 are both parallel to the optical axis X''', and this optical axis is perpendicular to the face 153.

A Laue diagram is produced under these conditions and the billet is rotated on the specimen-carrier until the [011] axis is perpendicular to face 1 and the [$\bar{1}$01] axis is perpendicular to face 2 of the specimen-carrier.

Figure 4B:
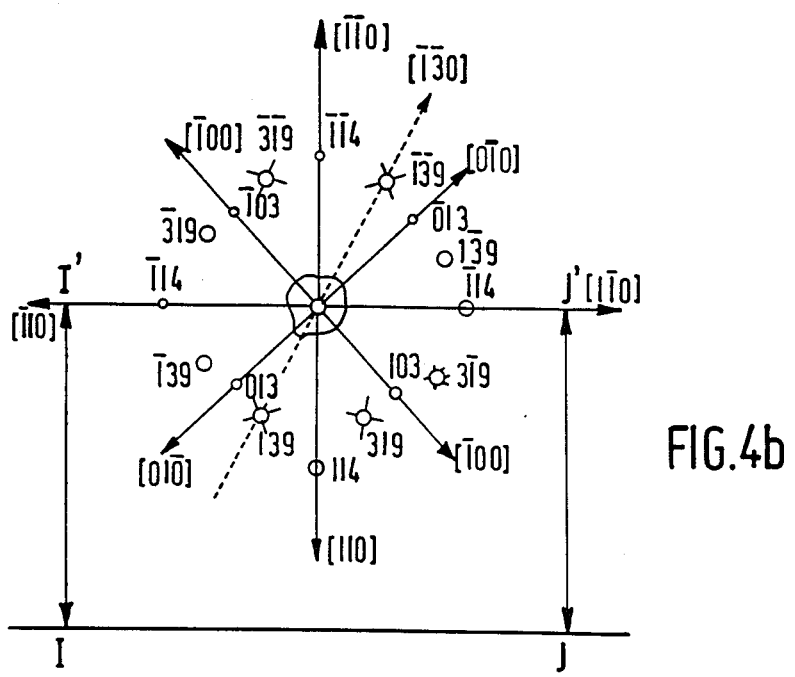

The determination of the [110] and [$\bar{1}$10] axes is carried out by successive measurements on Laue patterns such as that shown in FIG. 4b. Differences in the intensity of equivalent spots {139} indicate the [110] and [$1\bar{1}0$] directions for the (001) face.

As long as the billet has not been machined, and the measurement is carried out on the end face 153 of the billet, the axes have to be determined with respect to the frame of the film plane on which the pattern is recorded. This frame is represented by the straight Line IJ in FIG. 4b and is approximately parallel to the face 1 of the specimen-carrier.

The disorientation of the [$\bar{1}$10] axis with respect to the edge of the frame taken as reference is given by the relationship:

$$\Delta\theta = \frac{IJ' - JJ'}{IJ}$$

Using the indications provided by this measurement, a flat face 55 is machined at right angles to the [011] axis. The measurement can then be repeated by resting the flat face on the face 1 of the specimen-carrier, the face 153 being, furthermore, oriented in the same manner as previously.

Using successive measurements carried out on the face 153, the orientation of the flat face 55 is modified by machining until the accuracy of its orientation is of the order of ±1°.

Figure 4C:
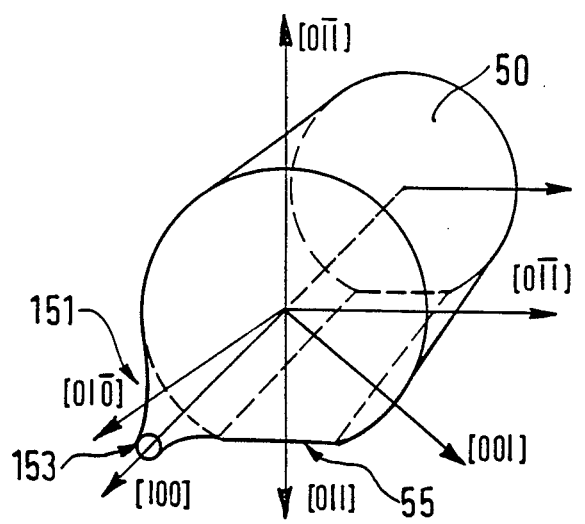

The billet is then machined to produce a cylinder 50 whose axis is parallel to the pulling axis, as shown in FIG. 4c.

From this operation onward, the measurements are made on Laue patterns produced by letting the x-ray beam fall onto a generatrix of the cylinder 50. For this purpose, this cylinder 50 is placed on the specimen-carrier 10 so that the flat face 55 rests on the face 1 and that a generatrix is supported against the face 2. The specimen-carrier is placed on the bench B so that the face 2 is perpendicular to the optical axis X''', and that the x-ray beam falls onto a generatrix of the cylinder, that is to say in a position defined as transverse.

Figure 4D:
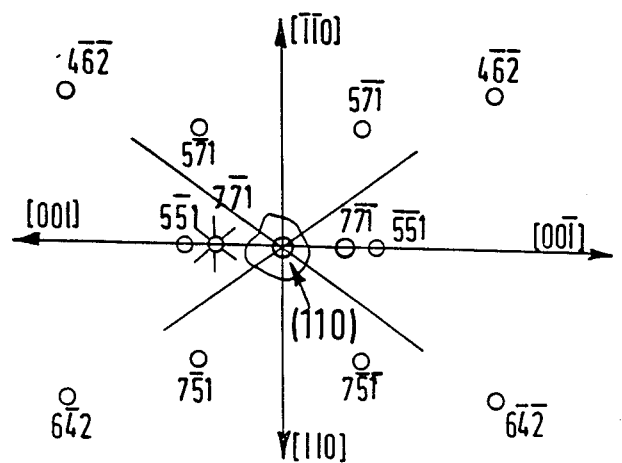

A Laue pattern such as is shown in FIG. 4d is obtained. To obtain an excellent accuracy in the determination of the [001] and [110] axes, it is no longer necessary to carry out the measurements with respect to the frame of the film plane, this being obviously highly inaccurate. The differences in the intensity of equivalent spots {771} determine the [001] and [00$\bar{1}$] directions for the planes (1$\bar{1}$0).

The accuracy of the measurements is determined by a double measurement carried out by rotating the cylinder 50 through 180° on the specimen-carrier 10, the flat face 55 continuing to rest on the face 1. This double measurement makes it possible to check the reproducibility of the patterns with respect to the reference edge of the film-plane support, but as a relative measurement and not as an absolute measurement.

An accuracy better than 0.1° is obtained without any complex adjustment, since once the optical bench is aligned with respect to the collimator and the source, the only operations consist purely and simply of placing the specimen-carrier in the required direction on the optical bench and then supporting the specimen against the faces 1 and 2.

Such measurements can be carried out systematically and quickly in industrial manufacture.

When the optimum orientation of the axis of the cylinder and of the end faces is obtained, thin discs 60 are cut from the cylinder 50 at right angles to the axis. The flat face 55 produced on the cylinder forms, as already seen, a cut reference facet 65 on each disc.

A second part 20 is then placed next to the specimen-carrier 10 to produce the measurement of orientation of the faces of the thin discs cut from the cylinder.

Figure 4E:
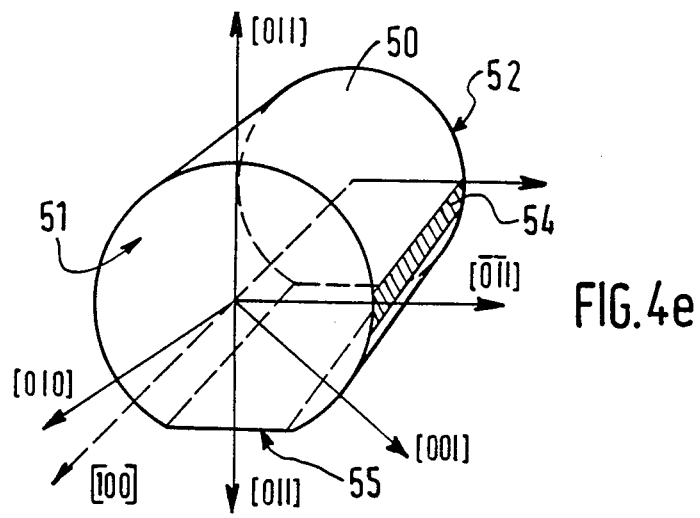
Figure 4F:
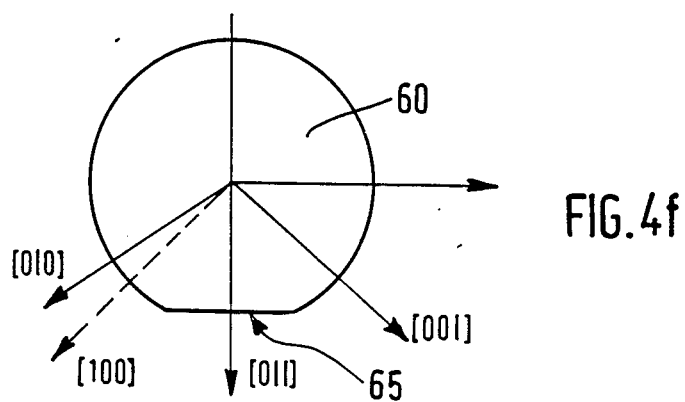
Figure 5A:
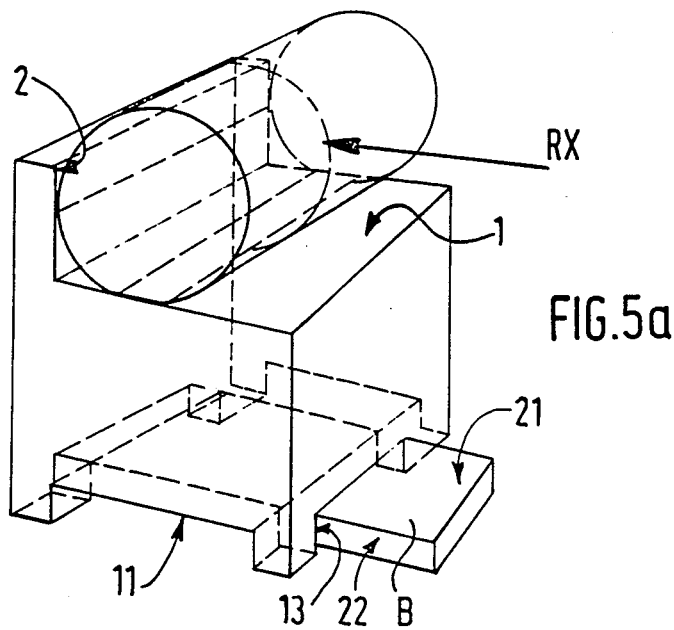
Figure 5B:
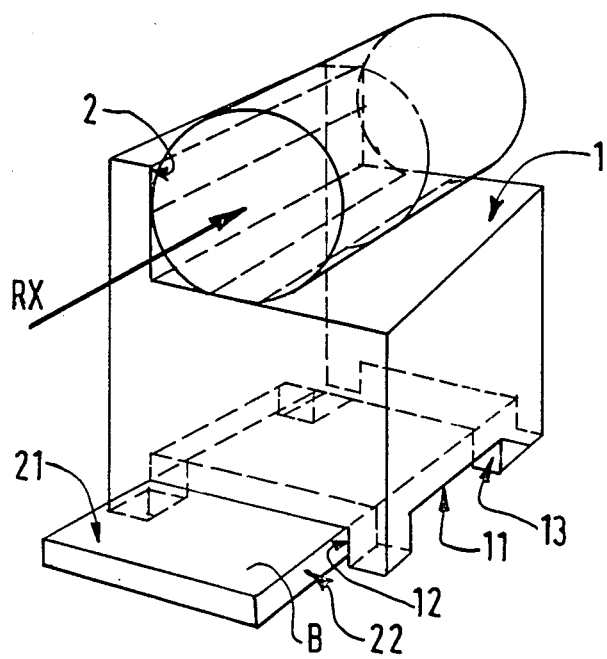

A thin disc of this kind is shown in FIG. 4f.

As shown in FIG. 6a, the second part of the specimen-carrier, or disc-carrier 20, consists of a parallelepipedal body 9 having reference planes 31, 32 and 33, which are perpendicular to each other.

During a measurement, the planes 31 and 32 of the disc-carrier are intended to be made to coincide with the planar faces 1 and 2 of the specimen-carrier, respectively.

Figure 1:
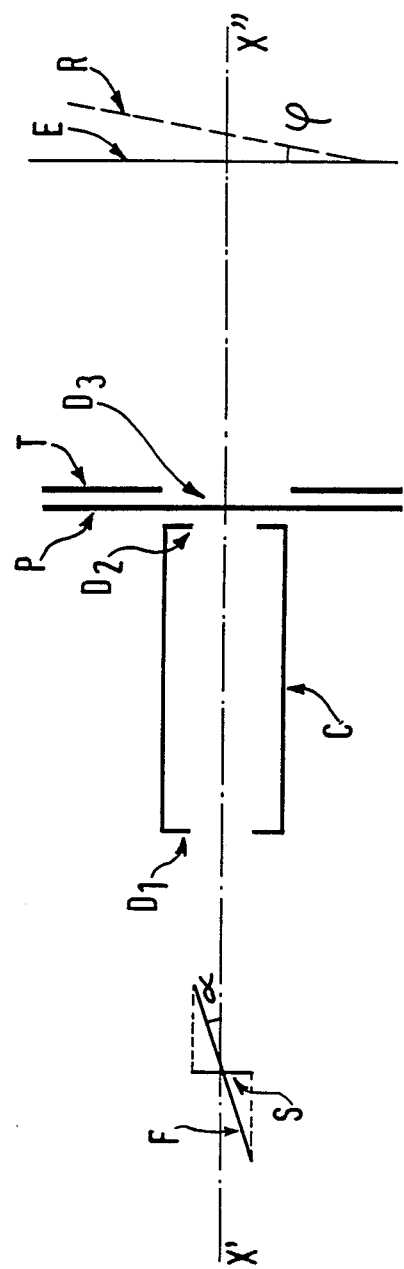
Figure 2A:
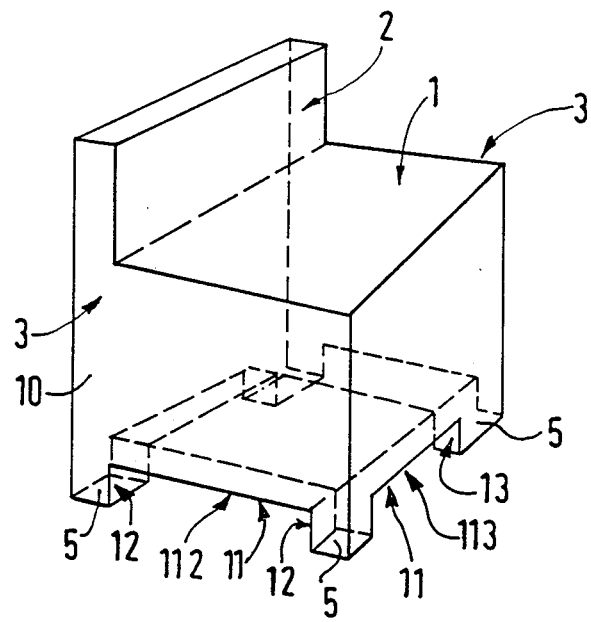
FIG. 2b shows in cross-section the specimen-carrier according to the invention in an example of embodiment adapted to receive cylindrical monocrystalline specimens of diameter $W_{10}=2$ inches, that is to say approximately 51 mm $= W_{10}$.
FIG. 2c shows in cross-section the specimen-carrier according to the invention in an example of embodiment adapted to receive cylindrical monocrystalline specimens of diameter $W'_{10}=3$ inches, that is to say approximately 76 mm $= W'_{10}$.
FIG. 2d shows either of the specimen-carriers for either of these adaptations, viewed from the side of the back-plate formed by the opposite side of the planar face 2.
Figure 2B:
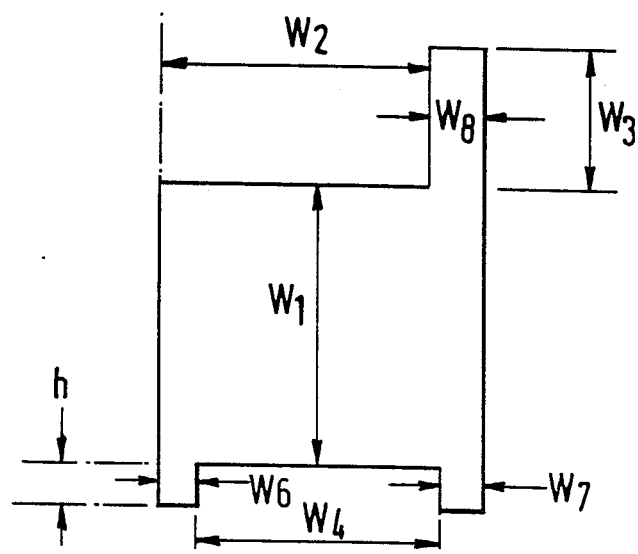
Figure 2C:
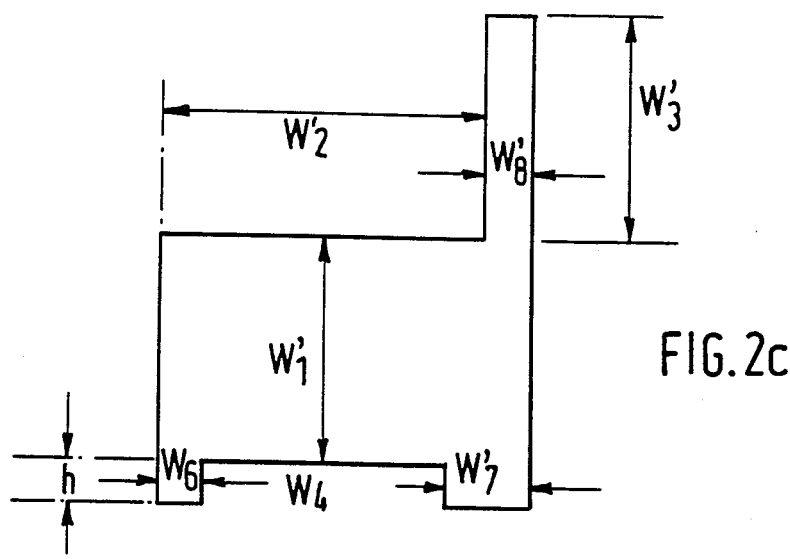
Figure 2D:
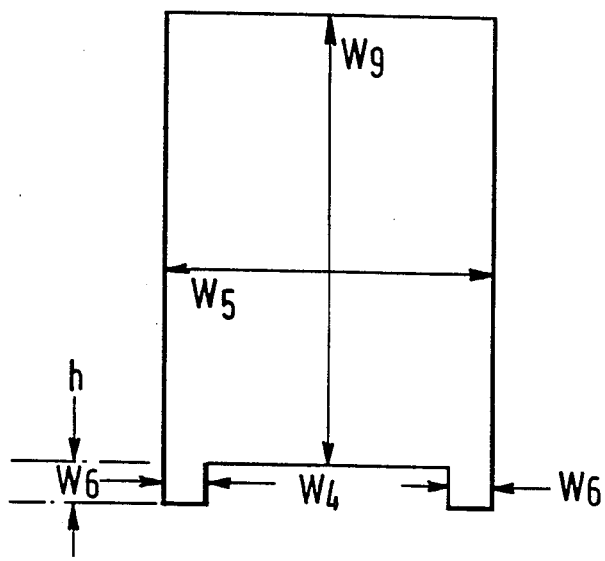
Figure 3A:
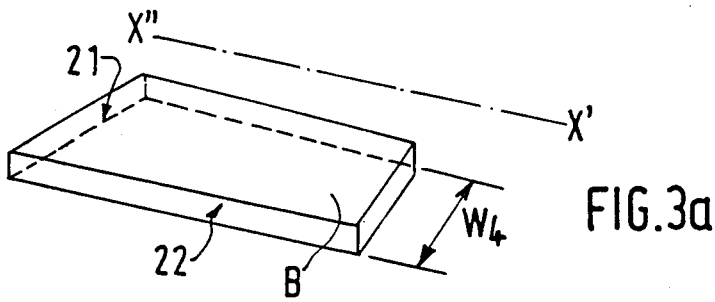
Figure 3B:
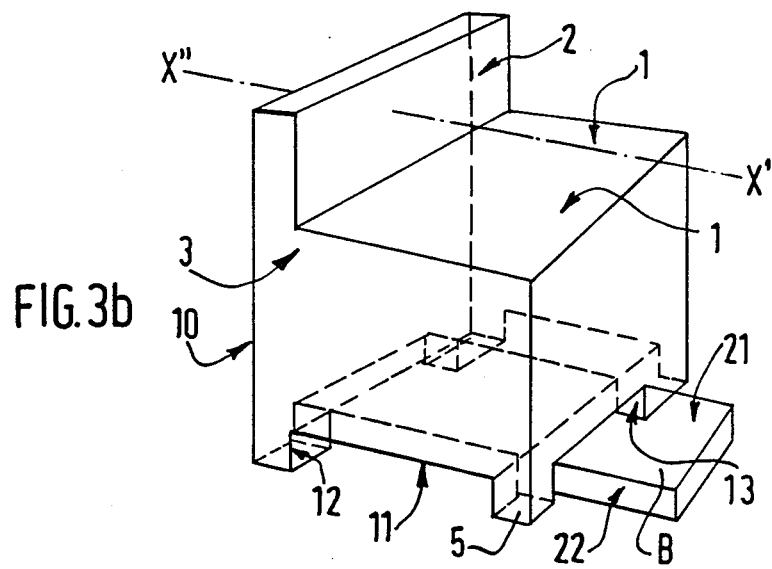
Figure 3C:
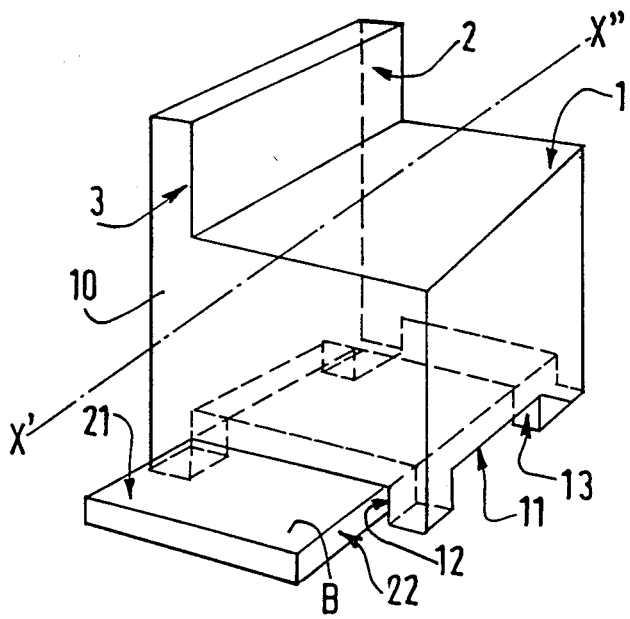

This is why, in the case where the specimen-carrier conforms to FIG. 2b, the planes 31 and 32 of the disc-carrier have the dimensions $W_5 \times W_{10}$, and in the case where the specimen-carrier conforms to FIG. 2c, the planes 31 and 32 have the dimensions $W_5 \times W'_{10}$.

The body 9 also comprises a central cavity 36 to enable it to be connected to a vacuum device, not shown, for example by means of a tube 46.

This body 9 is also equipped, in parallel to the reference plane 33, with a flange 8 of a dimension which is relatively immaterial, $W_{11}$ or $W'_{11}$, merely overlapping beyond the faces 31 and 32 so that this flange 8 blocks the disc-carrier against the side 3 of the specimen-carrier 10, when the body 9 is in place on the specimen-carrier.

This flange 8 is provided with a square cavity which uncovers the planar face 43 parallel to the reference plane 33. This planar face 43 has dimensions $W_{10} \times W_{10}$ to receive discs of diameter $W_{10}$, or dimensions $W'_{10} \times W'_{10}$ for discs of diameter $W'_{10}$.

The depth of the square cavity, d, is equal to the thickness of a disc 60. This planar face 43 is fashioned so that its planarity is highly accurate. In addition, a plug of a substance which is both rigid and porous 26 is placed at the mouth of the cavity 36 which can be connected to a vacuum pump, so that the bottom of the cavity 36 is perfectly planar.

The flange 8 is also provided with fastening tabs 27 and 28 held, for example, by means of screws.

In the measuring position, the disc 60 cut from the cylinder 50 is placed in the square cavity against the planar face 43, is held by the tabs 27 and 28 and is pulled flat against the bottom of the square cavity by the application of vacuum to the cavity 36. The plug 26 of a rigid and porous substance prevents the distortion of the disc 60 when this vacuum is applied.

The body 9 is positioned on the specimen-carrier so that its faces 31 and 32 coincide with the faces 1 and 2 of the specimen-carrier, respectively.

The specimen-carrier is then placed on the optical bench B so that the optical axis X'X" is parallel to faces 1 and 2, and perpendicular to the disc 60 placed in the cavity 43, that is to say in the position defined as lengthwise.

The cut facet 65 is supported against one of the sides 41 or 42 of the cavity 43. These sides 41 and 42 form planar faces parallel to the planar faces 1 and 2 respectively and serve as a reference for the production of the Laue pattern.

To obtain a high accuracy of the measurement, a double measurement is carried out, by turning the disc over to reverse its faces on the disc-carrier. This reversal makes it possible to give the values of the instrument constant and of the disorientation, from the difference of the semitotal of the angles between the spots of the same index.

Table II gives the dimensions of the disc-carrier, as an example of implementation.

TABLE II

| 2 inches ≃ 51 mm application | 3 inches ≃ 76 mm application |
| --- | --- |
| $W_{10}$ = 51 mm | $W'_{10}$ = 76 mm |
| $W_5$ = 76 mm | $W_5$ = 76 mm |
| $W_6$ = 10 mm | $W_6$ = 10 mm |
| d = 1 mm | d = 1 mm |
| $W_{11}$ = 71 mm | $W'_{11}$ = 96 mm |
| $W_{12}$ = 91 mm | $W'_{12}$ = 116 mm |
| $W_{13}$ = 10 mm | $W'_{13}$ = 10 mm |

The material of construction of the disc-carrier 20 may be chosen from the materials mentioned as materials of construction of the specimen-carrier.

The material of construction of the rigid and porous plug 26 may advantageously be sintered bronze.

A small flat face may additionally be produced on the bulk monocrystalline cylinder 50, at 90° to the large flat face. This small flat face makes it possible, therefore, to determine a third crystallographic reference.

As shown in FIG. 4e, it was chosen to produce the small flat face 54 on the cylinder of gallium arsenide at right-angles to the $[0\bar{1}1]$ axis.

These conventions, namely, in the case of gallium arsenide, pulling axis along [100]

plane of the large flat face perpendicular to the [011] axis plane of the small flat face perpendicular to the $[0\bar{1}1]$ axis, constitute an example of preferred embodiment for this material, because the large flat face then has the simplest indices, and because the small flat face is deduced from the large flat face by a rotation of 90° in the trigonometric sense.

It is obvious, however, that other conventions may be adopted without altering the structure of the specimen-carrier device according to the invention, or the process for performing a measurement with the aid of this device, and this demonstrates its advantage.

What is claimed is:

1. A device for measuring orientation of bulk monocrystalline materials comprising
   polychromatic X-ray source means for producing X-rays,
   photographic film support means for supporting film,
   collimator means disposed in the path of said X-rays between said source means and said film support means,
   a Laue chamber containing said X-ray source means, said film support means, and said collimator means, said collimator means defining the optical axis of said Laue chamber,
   first means for supporting a bulk specimen, second means for aligning said Laue chamber and said first means, and third means for determining orientation of said bulk specimen relative to crystallographic axes, wherein said first means includes at least one specimen carrier means for carrying said bulk specimen, said specimen carrier means comprising a first planar surface to receive said bulk specimen and a second planar surface perpendicular to said first planar surface to immobilize said bulk specimen, wherein said specimen carrier means further comprises a first reference planar surface parallel to said first planar surface, a second reference planar surface parallel to said second planar surface, and a third reference planar surface perpendicular to both said first reference planar surface and said second reference planar surface, wherein said second means includes an optical bench comprising at least two planar reference faces, said at least two planar reference faces being parallel to said optical axis of said Laue chamber, and wherein said first means and said second means are disposed to provide said third means, said at least two planar reference faces of said optical bench being disposed during measurements either to be parallel to said first and second reference planar surfaces of said specimen carrier means or to be parallel to said first and third reference planar surfaces of said specimen carrier means.

2. A device according to claim 1, wherein said first planar surface and said second planar surface of said specimen carrier are deposited at a distance from said optical axis when said at least two planar reference faces of said optical bench are disposed parallel to said first and second reference planar surfaces of said specimen carrier, said distance being substantially equal to a mean radius of said bulk specimen.

3. A device according to claim 1, wherein said first means further includes disc carrier means for carrying a crystallographic oriented slice of said bulk specimen, said disc carrier means including a structure comprising a first planar face, a second planar face perpendicular to said first planar face for supporting and immobilizing said slice, and a third planar face perpendicular to said first and second planar faces for receiving a face of said slice, wherein said structure further comprises a first parallel reference planar surface and a second parallel reference planar surface, and wherein said disc carrier means interacts with said specimen carrier means and said second means to provide fourth means for determining orientation of said slice, said first and second parallel reference planes of said structure resting against said first and second planar surfaces of said specimen carrier means during measurement, and said at least two planar reference surfaces of said optical bench supporting said first and third reference planar surfaces of said specimen carrier means.

4. A process for producing a semiconductor device from a bulk monocrystalline billet of a semiconductor material having an axis of crystal growth parallel to a crystallographic axis, said process comprising the steps of growing at least a substrate disc oriented along a crystallographic axis, locating crystallographic planes of said substrate disc by a device for measuring orientation of bulk monocrystalline materials, wherein said device includes polychromatic X-ray source means for producing X-rays, photographic film support means for supporting film, collimator means disposed in the path of said X-rays between said source means and said film support means, a Laue chamber containing said X-ray source means, said film support means, and said collimator means, said collimator means defining the optical axis of said Laue chamber, first means for supporting a bulk specimen, second means for aligning said Laue chamber and said first means, and third means for determining orientation of said bulk specimen relative to crystallographic axes, wherein said first means includes at least one specimen carrier means for carrying said bulk specimen, said specimen carrier means comprising a first planar surface to receive said bulk specimen and a second planar surface perpendicular to said first planar surface to immobilize sail bulk specimen, wherein said specimen carrier means further comprises a first reference planar surface parallel to said first planar surface, a second reference planar surface parallel to said second planar surface, and a third reference planar surface perpendicular to both said first reference planar surface and said second reference planar surface, wherein said second means includes an optical bench comprising at least two planar reference faces, said at least two planar reference faces being parallel to said optical axis of said Laue chamber, and wherein said first means and said second means are disposed to provide said third means, said at least two planar reference faces of said optical bench being disposed during measurements either to be parallel to said first and second reference planar surfaces of said specimen carrier means to be parallel to said first and third reference planar surfaces of said specimen carrier means, and machining reference faces on said substrate disc parallel to given ones of said crystallographic planes.

5. A process according to claim 4, further comprising the steps of (a) locating a characteristic crystal plane by placing a bulk monocrystalline billet on said specimen carrier means to rest against both said first and second planar surfaces, wherein said axis of crystal growth is parallel to said first and second planar surfaces, and by placing said specimen carrier means on said optical bench with said first and second reference planar surfaces of said specimen carrier means resting against said at least two planar reference faces of said optical bench, said crystallographic growth axis coinciding with said optical axis, wherein an X-ray diffraction pattern is produced by starting with a face of said billet perpendicular to said growth axis, (b) machining a first reference face along a plane parallel to said axis of crystal growth, (c) measuring any disorientation after said step (b) by placing said bulk monocrystalline billet on said specimen carrier means with said first reference face resting on said first planar surface, by resting a generatrix of said bulk monocrystalline billet against said second planar surface, said growth axis being parallel to said first and second planar surfaces, and by placing said specimen carrier means on said optical bench with said first and third reference planar surfaces parallel to said at least two planar reference faces of said optical bench, said growth axis being perpendicular to said optical axis, said step (c) being carried out on a diagram of X-ray diffraction by a face parallel to said generatrix and parallel to said growth axis, (d) machining said bulk monocrystalline billet into a cylinder with an axis of symmetry parallel to said growth axis, modifying machining of said first reference face if necessary, and machining bases of said cylinder at right angles to said growth axis, (e) measuring any existing disorientation of said cylinder bases and said first reference face by repeating steps (a) and (c), (f) remachining said first reference face and said cylinder bases according to measurements in step (e) until a required accuracy is obtained relative to their orientation, (g) cutting off a disc in parallel to said cylinder bases to form a substrate of said semiconductor material, and (h) measuring any existing disorientation of said disc by placing said disc on said disc carrier means, by placing said disc carrier means on said specimen carrier means, and by again producing an X-ray diffraction pattern according to step (a).

6. A process according to claim 5, further comprising before said step (g) the steps of (i) locating a crystal plane perpendicular to said first reference face and parallel to said growth axis according to step (a), (j) machining a second reference face along said crystal plane in step (i), said second reference face being smaller than said first reference face, and (k) measuring any disorientation of said second reference face according to step (c), and modifying said machining step of (j) until a required accuracy has been obtained.

7. A process according to claim 5 or claim 6, wherein said measurements of disorientation is carried out by using two diffraction patterns obtained by rotating said specimen through 180° in parallel to said first reference face.

* * * * *